(12) United States Patent
Soe et al.

(10) Patent No.: US 6,403,570 B1
(45) Date of Patent: Jun. 11, 2002

(54) METHOD OF CURING AN INJURY TO A SKIN SURFACE

(75) Inventors: Gilbu Soe; Motonori Aoshima; Koichi Takada, all of Tokyo (JP)

(73) Assignee: Hogy Medical Co., Ltd., Tokyo (JP)

( * ) Notice: Subject to any disclaimer, the term of this patent is extended or adjusted under 35 U.S.C. 154(b) by 0 days.

(21) Appl. No.: 09/688,575

(22) Filed: Oct. 16, 2000

Related U.S. Application Data

(62) Division of application No. 09/312,416, filed on May 14, 1999, now Pat. No. 6,214,808.

(30) Foreign Application Priority Data

May 15, 1998 (JP) ............................................ 10-133289

(51) Int. Cl.⁷ ............................................ A61K 31/715
(52) U.S. Cl. ......................................................... 514/57
(58) Field of Search ............................................ 514/57

(56) References Cited

FOREIGN PATENT DOCUMENTS

GB        1249618      * 10/1971

* cited by examiner

*Primary Examiner*—Kevin E. Weddington
(74) *Attorney, Agent, or Firm*—Darby & Darby

(57) ABSTRACT

A hemostatic agent, an agent for promoting cellular adhesion and an agent for curing an injury, each comprising an alkali or alkali earth metal salt of carboxylmethyl cellulose, and a pharmaceutically acceptable carrier are disclosed.

5 Claims, 1 Drawing Sheet

METHOD OF CURING AN INJURY TO A SKIN SURFACE

This is a division of application Ser. No. 09/312,416 filed May 14, 1999 now U.S. Pat. No. 6,214,808.

BACKGROUND OF THE INVENTION

1. Field of the Invention

The present invention relates to a hemostatic agent comprising an alkali metal or alkali earth metal salt of carboxylmethyl cellulose. The present invention also relates to an agent for promoting cellular adhesion and an agent for curing an injury, which agent contains an alkali metal or alkali earth metal salt of carboxylmethyl cellulose. The hemostatic agent, the agent for promoting cellular adhesion, and the agent for curing an injury according to the present invention are assimilatable in a living body, and may be sprinkled on or applied to an injury to a skin surface or an injury at a site of an intracorporeal tissue to accelerate blood coagulation and cellular adhesion.

2. Description of the Related Art

Three types of hemostatic agents for injuries are mainly known; an oxidized cellulose preparation, a gelatin preparation and a microfibrous collagen preparation, and these are used as a drug or medical supply. The oxidized cellulose preparation includes polygluconic anhydrides as a main component. The polygluconic anhydride has a strong affinity for hemoglobin, and thus forms a salt with hemoglobin whereby a hemostatic effect is exhibited. It is believed that the above effect to promote coagulation is not due to a blood coagulation process in a living body but to a physical effect. That is, the oxidized cellulose preparation is swollen by an infiltration of blood to promote a formation of brown or black gelatinous clots or coagula, which act as a hemastatic auxiliary agent for a bleeding region. The oxidized cellulose preparation is assimilated in the course of about 2 weeks. The microfibrous collagen preparation contains, as a main component, naturally occurring collagen extracted from bovine dermis or the like, so that it forms a platelet-agglutination upon coming into contact with blood to conduct a hemostasis.

SUMMARY OF THE INVENTION

However, the oxidized cellulose preparation does not act directly on the blood coagulation process, and the coagulating effect is poor. Further, a complete assimilation in a living body takes about 2 weeks, and thus it may cause inflammation or conglutination at the site where the oxidized cellulose preparation is applied.

The gelatin preparation has a less assimilability than the oxidized cellulose preparation. Also, the gelatin preparation contains materials taken from animals, and there is a high possibility of the transference of infectious diseases, such as a prion disease (or spongiform encephalopathy).

Regarding the microfibrous collagen preparation, a complete assimilation thereof takes at least one month, and thus the preparation might cause inflammation or conglutination in an injured site. Further, the materials are taken from a bovin, and thus there is a danger of the occurrence of the prion disease or infectious diseases caused by an unknown virus.

In a hemostasis carried out by conventional hemostatic agents as above, defects occur in that the intracorporeal assimilatability of the hemostatic agents is low, the hemostatic agents cause inflammation, conglutination and so on, and the possibility of the occurrence of unknown infectious diseases exists.

The present inventors engaged in studies to solve the above problems and as a result found that sodium or calcium of carboxylmethyl cellulose exhibits a hemostatic function, and a function to promote cellular adhesion, and can act as a novel hemostatic agent for covering an injury.

Accordingly, the object of the present invention is to remedy the defects of prior art and to provide a hemostatic agent wherein a hemostatic action provided is very rapid and effective, an inflammation reaction rarely occurs, an intracorporeal assimilatability is excellent, a curing effect of injuries is high, and an infection by an unknown pathogen can be completely prevented.

Other objects and advantages will be apparent from the following description.

In accordance with the present invention, there is provided a hemostatic agent comprising an alkali metal or alkali earth metal salt of carboxylmethyl cellulose, and a pharmaceutically acceptable carrier.

Further, in accordance with the present invention, there is provided an agent for promoting cellular adhesion, comprising an alkali metal or alkali earth metal salt of carboxylmethyl cellulose, and a pharmaceutically acceptable carrier.

Still further, in accordance with the present invention, there is provided an agent for curing an injury, the agent comprising an alkali metal or alkali earth metal salt of carboxylmethyl cellulose, and a pharmaceutically acceptable carrier.

DESCRIPTION OF THE PREFERRED EMBODIMENTS

Figure 1:
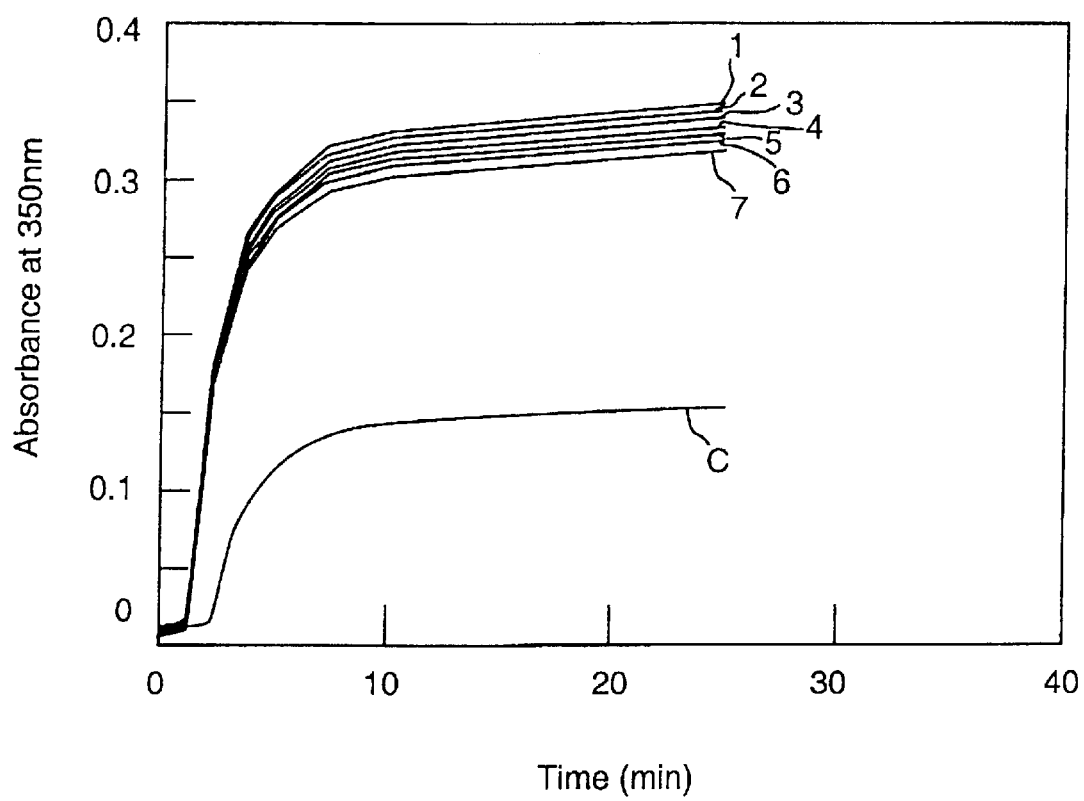
FIG. 1 illustrates an effect of sodium carboxylmethyl cellulose on an aggregation reaction of fibrin monomers.

An alkali metal salt or an alkali earth metal salt of carboxylmethyl cellulose (hereinafter sometimes referred to as a carboxylmethyl cellulose salt) which may be used in the present invention is an alkali metal salt or an alkali earth metal salt of a polyfunctional carboxylmethyl ether of a cellulose which is etherified with carboxylmethyl groups at a part or all of the hydroxy groups.

The degree of etherification with carboxylmethyl groups is not particularly limited, but is preferably 0.5 to 1.5, more preferably 0.6 to 0.95, and most preferably 0.6 to 0.8, to ensure an appropriate water-solubility. The position of the hydroxyl group to be etherified is not particularly limited, that is, one or more hydroxy groups at 2-, 3- and/or 6-positions may be etherified.

The average molecular weight of the carboxylmethyl cellulose salt is not particularly limited, but is preferably 100 kD to 100000 kD, more preferably 10 kD to 2000 kD, and most preferably 200 kD to 1000 kD. A low molecular weight carboxylmethyl cellulose salt may be prepared by etherifying a low molecular weight cellulose and converting the etherified cellulose to a salt thereof, or generally, by etherifying a high molecular weight cellulose, and then converting the etherified cellulose to a salt thereof and degrading the salt, or degrading the etherified cellulose and converting the degraded cellulose to a salt thereof. The degradation may be carried out by a known method, such as an electron ray irradiation or γ-ray irradiation. The degradation by the electron ray irradiation or γ-ray irradiation is preferable, because the product is thus sterilized at the same time.

The content of the alkali metal or alkali earth metal in the carboxylmethyl cellulose salt used in the present invention is not particularly limited, but is preferably 5–13% by weight, more preferably 5–10% by weight, and most preferably 6–8% by weight. The alkali metal is, for example, sodium, potassium or lithium, and the alkali earth metal is, for example, calcium or magnesium. The carboxylmethyl cellulose salt used in the present invention may contain one or more alkali metal or alkali earth metal as above.

The hemostatic agent of the present invention may be applied in any form to a site in need of hemostasis, i.e., a stopping or controlling of bleeding. For example, the hemostatic agent may be applied in a solid form (such as a powder, granule, film, sponge, or a bulk), a liquid form (such as a solution), or a paste form, directly to the site in need of hemostasis or via a medical instrument such as a catheter to an intracorporeal site.

The agent for promoting cellular adhesion or the agent for curing an injury according to the present invention may be applied in any form, and in any manner, to a site in need of a promoting of cellular adhesion or in need of a curing of an injury, as the hemostatic agent.

The site in need of a controlling of bleeding, a promoting of cellular adhesion or a curing of an injury is, for example, a site of a wound or injury, an opening incised during a surgical operation, or a puncture site remaining open after removing a catheter or dialysis needle The hemostatic agent, the agent for promoting cellular adhesion or the agent for curing an injury according to the present invention may be formulated into a form suitable by a site to which it is to be applied, and may contain one or more carriers suitable for the formulation and known to those skilled in the art.

The functional mechanism of the hemostatic agent according to the present invention has not been fully elucidated, but can be speculated upon as follows; it should be understood that the present invention is not limited by the following speculation.

Circulating blood exercises physiological functions while always maintaining a flowability. When a blood system encounters a rupture, the circulating blood loses flowability and is gelled. Hemostasis contains two mechanisms, i.e., a primary hemostasis wherein platelets or thrombocytes mainly take part, and a secondary hemostasis wherein plasma components take part. Further, the secondary hemostasis includes an intrinsic coagulation and an extrinsic coagulation. An action exerted upon the primary hemostasis can be determined by measuring the extent of acceleration of the platelet agglutination. It has been found that the carboxylmethyl cellulose salt remarkably accelerates the platelet agglutination by adenosine diphosphate (ADP), whereas the carboxylmethyl cellulose salt does not activate intrinsic or extrinsic aggregating factors in the secondary hemostasis, but the carboxylmethyl cellulose salt remarkably accelerates aggregation from fibrin monomers to fibrin polymers which corresponds to a final step in an intrinsic and extrinsic aggregation cascade.

As above, the carboxylmethyl cellulose salt accelerates the agglutination of platelets or thrombocytes via fibrinogen or fibrin monomers, and also accelerates the aggregation of fibrin monomers to fibrin polymers. This implies that the carboxylmethyl cellulose salt acts physically on a fibrinogen molecule or fibrin monomer molecule to thereby exhibit a hemostatic function.

Further, as shown in the Examples, the carboxylmethyl cellulose salt remarkably accelerates cellular adhesivity of NIH3T3 cells in the presence of a minimum concentration exhibiting a cellular adhesion of a cellular adhesive protein, such as fibronectin, vitronectin, laminin, collagen or a fibrin monomer. Therefore, the carboxylmethyl cellulose salt can be used as an agent for promoting cellular adhesion.

Still further, as shown in the Examples, the carboxylmethyl cellulose salt has an excellent effect of curing injuries, and thus can be used as an agent for curing an injury.

Therefore, the carboxylmethyl cellulose salt can be used as a hemostatic agent having a promoting action on cellular adhesion and a curative action on an injury.

The carboxylmethyl cellulose salt is highly assimilatable in a living body, and thus can be used as a covering material for an injury to a skin surface or an intracorporeal wound.

As above, it has been found that the carboxylmethyl cellulose salt is very useful as a hemostatic agent or as a material for a skin surface or an intracorporeal part of the body, and has a wide applicability as a hemostatic agent or material.

EXAMPLES

The present invention will now be further illustrated by, but is by no means limited to, the following Examples.

Preparation Example 1
Preparation of Low Molecular Weight CMC-Na's

Carboxylmethyl cellulose sodium salts (CMC-Na's) having various molecular weights were prepared by an electron ray irradiation. More particularly, solid sodium carboxymethyl cellulose (the degree of etherification=0.8; the content of sodium=8% by weight) was exposed to electron rays of 20 kGy, 40 kGy, 60 kGy, 80 kGy, or 100 kGy at 10 MeV by CIRCE-II linear accelerator (CGR-McV). The term "Gy" means gray, a unit of a radiation energy, and 1 Gy corresponds to 1 J/kg.

Non-irradiated or irradiated sodium carboxylmethyl cellulose was dissolved in distilled water, and lyophilized. Then, the lyophilized product was crushed in a mortar, and the resulting powder was used in the determination of molecular weight and in the following Examples.

The molecular weights were determined as follows:

The powder of non-irradiated or irradiated sodium carboxylmethyl cellulose was dissolved in a 50 mM tris-HCl buffer containing 0.15 M NaCl, and applied in a Sepharose CL-6B column equilibrated with the same buffer to carry out a molecular sieve chromatography. Sodium carboxylmethyl cellulose was detected by a phenol-sulfuric acid method. The results are shown in Table 1.

TABLE 1

| | Non-irradiated | Irradiated with electron rays | | | | |
| --- | --- | --- | --- | --- | --- | --- |
| | | 20 kGy | 40 kGy | 60 kGy | 80 kGy | 100 kGY |
| Molecular weight | 2000 kD | 1000 kD | 800 kD | 600 kD | 400 kD | 200 kD |

Table 1 shows that sodium carboxylmethyl cellulose can be degraded to a low molecular weight compound by an irradiation of electron rays.

Example 1
Activity for Aggregating Fibrin Monomers

Powdery non-irradiated or irradiated sodium carboxylmethyl cellulose (CMC-Na) prepared in Preparation Example 1 was dissolved in a 20 mM imidazole buffer containing 0.15M NaCl, to the concentration of 10 mg/ml.

To 0.5 ml of the resulting solution, was added 20 µl of a fibrin monomer solution (A280 nm=6) prepared by dissolving fibrin monomers in 20 mM acetic acid, and admixed for 5 seconds. Thereafter, the mixture was poured into a quartz cell having an optical path of 1 cm. After 20 seconds of adding fibrin monomers, an absorbance at 350 nm was measured every 30 seconds for 25 minutes. As a control test, the same procedure was repeated except that the powdery sodium carboxylmethyl cellulose was not used. The absorbance was measured by an ultraviolet-visible light spectrophotometer (U-3210; Hitachi Ltd.). The results are shown in FIG. 1, wherein the curve 1 is the result in the presence of CMC-Na not irradiated with electron rays, the curve 2 is the result in the presence of CMC-Na irradiated with 10 kGy, the curve 3 is the result in the presence of CMC-Na irradiated with 20 kGy, the curve 4 is the result in the presence of CMC-Na irradiated with 40 kGy, the curve 5 is the result in the presence of CMC-Na irradiated with 60 kGy, the curve 6 is the result in the presence of CMC-Na irradiated with 80 kGy, and curve 7 is the result in the presence of CMC-Na irradiated with 100 kGy). Further, the curve C shows the result of the control test.

FIG. 1 shows that sodium carboxylmethyl cellulose remarkably accelerates the aggregation of fibrin monomers, independently of the irradiation of electron rays, i.e., in its wide molecular weight range.

Example 2

Activity to Promote Cellular Adhesion

An activity of sodium carboxylmethyl cellulose (CMC-Na) to promote cellular adhesion of various cellular adhesive proteins when added thereto was examined.

A 96-well plate was coated with a cellular adhesive protein, i.e., fibronectin, vitronectin, laminin, collagen or fibrin at various concentrations, and 5000 cells of NIH-3T3 were poured thereon. After 6 hours, cells adhered to the protein were counted. A minimum concentration where the cellular adhesive proteins exhibited a cellular adhesion (minimum cellular-adhesive concentration) was determined.

Then, sodium carboxylmethyl cellulose (CMC-Na) was added in a concentration of 10 mg/ml to a buffer containing the minimum cellular-adhesion concentration of the cellular adhesive proteins, and a 96-well plate was coated with the resulting solution. The same procedure as above was repeated to count the cells adhered to the proteins. The results are shown in Tables 2 and 3.

TABLE 2

| Cellular adhesive proteins | Minimum cellular-adhesive concentration ($\mu$g/ml) | Cells adhered without CMC-Na |
|---|---|---|
| fibronectin | 0.1 | 20 |
| vitronectin | 0.5 | 10 |
| laminin | 0.1 | 12 |
| collagen I | 0.1 | 5 |

TABLE 2-continued

| Cellular adhesive proteins | Minimum cellular-adhesive concentration ($\mu$g/ml) | Cells adhered without CMC-Na |
|---|---|---|
| collagen III | 0.1 | 8 |
| fibrin | 0.1 | 10 |

TABLE 3

| Cellular adhesive proteins | Cells adhered with CMC-Na Electron ray irradiation (kGy) | | | | | |
|---|---|---|---|---|---|---|
| | 0 | 20 | 40 | 60 | 80 | 100 |
| fibronectin | 60 | 65 | 70 | 62 | 68 | 60 |
| vitronectin | 50 | 48 | 42 | 46 | 53 | 58 |
| laminin | 36 | 40 | 42 | 38 | 42 | 46 |
| collagen I | 25 | 30 | 26 | 38 | 28 | 31 |
| collagen III | 32 | 30 | 28 | 33 | 36 | 33 |
| fibrin | 40 | 39 | 50 | 38 | 41 | 42 |

Tables 2 and 3 show that sodium carboxylmethyl cellulose remarkably increases the number of cells adhered, independently of the irradiation of electron rays, i.e., in its wide molecular weight range.

Example 3

Hemostatic and Injury-healing Effects

A hemostatic effect and an injury-healing effect of sodium carboxylmethyl cellulose were examined.

The hemostatic effect was evaluated in the light of the time required to stop bleeding. Livers of 10 mice were exposed by an abdominal operation, and two square portions (1 cm×1 cm, each) were cut from the surface of each liver to make wounded portions thereof. Powdery sodium carboxylmethyl cellulose was sprinkled on one wounded portion on the liver surface, but not sprinkled on another wounded portion. The two wounded portions were compared to ascertain the time required to stop bleeding.

An effect of healing wounded portions was examined as follows. After measuring the time required to stop bleeding, the abdominal region was closed. After one month, the liver was exposed again, and a pathological section was prepared from the portion where powdery sodium carboxylmethyl cellulose had been sprinkled on the wounded portion. The degree of healing was visually evaluated through a microscope. The degree of healing was evaluated in three stages as follows:

⊚: Same as normal
○: Slightly inflamed
X: inflamed and conglutinated.

The results are shown in Table 4.

TABLE 4

| Mice Nos. | 1 | 2 | 3 | 4 | 5 | 6 | 7 | 8 | 9 | 10 |
|---|---|---|---|---|---|---|---|---|---|---|
| Time (seconds) to stop bleeding without CMC-Na | | | | | | | | | | |
| | 132 | 140 | 250 | 180 | 100 | 180 | 120 | 138 | 185 | 201 |
| | | | | Average = 163; CV = 26% | | | | | | |
| Time (seconds) to stop bleeding with CMC-Na | | | | | | | | | | |
| | 30 | 28 | 33 | 40 | 38 | 32 | 33 | 26 | 34 | 33 |
| | | | | Average = 33; CV = 12% | | | | | | |

TABLE 4-continued

| Mice Nos. | 1 | 2 | 3 | 4 | 5 | 6 | 7 | 8 | 9 | 10 |
|---|---|---|---|---|---|---|---|---|---|---|
| Healing degree | | | | | | | | | | |
| | ○ | ○ | ○ | ○ | ○ | ○ | ○ | ○ | ○ | ○ |

(CV = Coefficient of variation)

Table 4 shows that sodium carboxylmethyl cellulose remarkably shortens the hemostatic time, and has an excellent hemostatic effect and injury-healing effect, because the wounded portion to which sodium carboxylmethyl cellulose had been added was almost completely recovered without inflammation.

Although the present invention has been described with reference to specific embodiments, various changes and modifications obvious to those skilled in the art are deemed to be within the spirit, scope, and concept of the invention.

What we claim is:

1. A method of curing an injury to a skin surface or an intracorporeal wound in need thereof, comprising applying to the skin surface or intracorporeal wound an alkali metal or alkali earth metal salt of carboxymethyl cellulose.

2. The method according to claim 1, wherein the carboxymethyl cellulose has an average molecular weight of 100 kD to 100,000 kD.

3. The method according to claim wherein the carboxymethyl cellulose has a degree of etherification of 0.5 to 1.5.

4. The method according to claim 1, wherein the content of the alkali metal or alkali earth metal is 5 to 13% by weight.

5. The method according to claim 1, wherein the injury is an opening incised during a surgical operation or a puncture site remaining open after removing a catheter or dialysis needle.

* * * * *